United States Patent [19]

Dietrich et al.

[11] 3,996,291

[45] Dec. 7, 1976

[54] PROCESS FOR THE PRODUCTION OF 4-HYDROXY-3,5-DIBROMOBENZALDEHYDE

[75] Inventors: Henri Dietrich, Arlesheim; Jörg Kallen, Allschwil; Gottfried Seifert, Muttenz, all of Switzerland

[73] Assignee: Ciba-Geigy Corporation, Ardsley, N.Y.

[22] Filed: Mar. 21, 1975

[21] Appl. No.: 560,831

[30] Foreign Application Priority Data

Mar. 25, 1974 Switzerland .................. 4105/74

[52] U.S. Cl. .................. 260/600 R; 260/623 H; 260/566 A
[51] Int. Cl.² .................. C07C 45/00
[58] Field of Search .................. 260/600, 623 H

[56] References Cited

UNITED STATES PATENTS 3,641,158    2/1972    Deinet et al. .................. 260/600

FOREIGN PATENTS OR APPLICATIONS 1,270,333    7/1961    France .................. 260/623 H

OTHER PUBLICATIONS

Ruderman, Ind. & Eng. Chem., Anal. Ed., vol. 18 (1946) 753–759.

*Primary Examiner*—Bernard Helfin
*Attorney, Agent, or Firm*—Harry Falber

[57] ABSTRACT

Production of 4-hydroxy-3,5-dibromobenzaldehyde reacting p-cresol with bromine, converting the 2,6-dibromo-p-cresol obtained as the first reaction product into 4-hydroxy-3,5-dibromobenzal bromide by further bromination and hydrolysing the latter.

7 Claims, 1 Drawing Figure

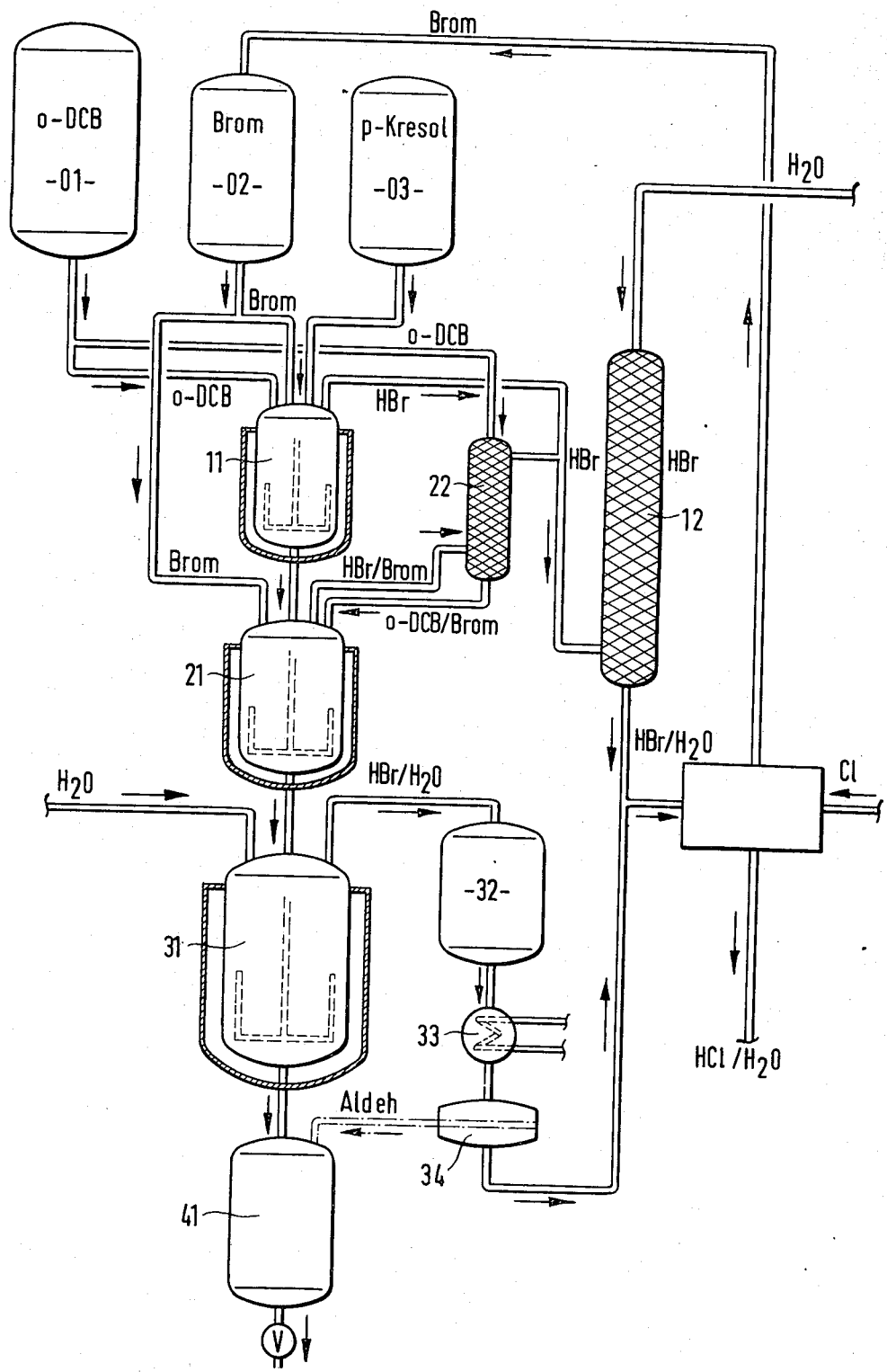

PROCESS FOR THE PRODUCTION OF 4-HYDROXY-3,5-DIBROMOBENZALDEHYDE

The present invention relates to a new process starting with p-cresol for the production of 4-hydroxy-3,5-dibromobenzaldehyde.

4-Hydroxy-3,5-dibromobenzaldehyde is a valuable starting material for producing herbicidal active substances. For example, the excellent herbicidally effective 0-(2,4-dinitrophenyl)-4-hydroxy-3,5-dibromobenzaldoxime can be obtained by reaction of 4-hydroxy-3,5-dibromobenzaldehyde, as starting material, with hydroxylamine, and subsequent condensation of the resulting oxime with 2,4-dinitrochlorobenzene.

4-Hydroxy-3,5-dibromobenzaldehyde has been produced starting with p-cresol hitherto by a process in which p-cresol was firstly converted into an ester, e.g. the carbonate or the phosphate, and this was reacted, by halogenation on the methyl group in the p-position, to give the corresponding benzal halide, which yielded on subsequent hydrolysis p-hydroxybenzaldehyde, which was then converted by bromination into the desired 4-hydroxy-3,5-dibromobenzaldehyde. This process is complicated not only on account of the large number of process stages required but also on account of the technical difficulties involved in carrying out the process, especially with regard to the hydrolytic splitting-off of the ester of 4-hydroxybenzal halide, since, in consequence of the necessary severe conditions, it is frequently the case that no more further-utilisable condensation products are formed.

The p-hydroxybenzaldehyde occurring as intermediate in the process discussed in the foregoing can be obtained also by reaction of p-cresol with chromic acid in a mixture of glacial acetic acid, acetic anhydride and sulphuric acid. In this reaction, there is firstly formed p-hydroxy-benzylidenediacetate, which is subsequently saponified to p-hydroxybenzaldehyde. On account of the high price of the required chromic acid and on account of the unsatisfactory yield, this process is not suitable for production on a commercial scale.

The process of the invention for the production of 4-hydroxy-3,5-dibromobenzaldehyde is characterised in that p-cresol is firstly converted by nucleus bromination into 2,6-dibromo-p-cresol. This is converted by side-chain bromination into 4-hydroxy-3,5-dibromobenzal bromide, and this is subsequently hydrolysed to 4-hydroxy-3,5-dibromobenzaldehyde.

The nucleus bromination of p-cresol can be performed in the presence or absence of inert solvents. To perform it in the presence of inert solvents is especially advantageous where it is desired to obtain a particularly pure final product. Suitable solvents are, in particular, halogenated hydrocarbons, e.g. chlorobenzene, o-dichlorobenzene, bromobenzene, chloroform and carbon tetrachloride. Nucleus bromination is performed in the presence of one of the aforementioned solvents at a temperature of between 0° and 50° C, especially between 20° and 30° C. Customary catalysts can be used for nucleus bromination, e.g. iron-3-chloride, but they are not essential. In the carrying out of nucleus bromination in the absence of an organic solvent, the reaction is performed in the melt. As a result, the reaction temperatures increase slightly to 45° to 55° C.

The side-chain bromination is advantageously performed immediately afterwards in the same reaction medium as that for the nucleus bromination. The side-chain bromination can be performed either at a temperature of between 30° and 180° C with irradiation by UV light or, purely thermally, at a temperature of between 120° and 180° C, preferably between 150° and 160° C.

Hydrolysis of 4-hydroxy-3,5-dibromobenzal bromide to 4-hydroxy-3,5-dibromobenzaldehyde is performed, after the addition of water to the reaction mixture, at 90° to 100° C. Where hydrolysis is carried out under pressure, it is also possible to use temperatures exceeding 100° C. On account of the heterogeneity of the reaction medium, it is advantageous to ensure a thorough mixing of the two phases by intensive stirring. In carrying out the process in an organic solvent, the proportion of organic solvent to water is advantageously between 2:1 and 1:2. These limits, however, can be exceeded either upwards or downwards.

After separation of the aqueous phase, the formed 4-hydroxy-3,5-dibromobenzaldehyde can be obtained by crystallisation. The resulting solution of 4-hydroxy-3,5-dibromobenzaldehyde can however be used directly for further reactions. Alternatively, the 4-hydroxy-3,5-dibromobenzaldehyde dissolved in the organic solvent can be extracted with diluted aqueous sodium hydroxide solution, and again precipitated from the resulting aqueous solution by acidification. The aqueous solution may also be directly further processed.

A preferred embodiment of the process of the invention comprises a process in which a solution of p-cresol in o-dichlorobenzene is used as starting material; nucleus bromination to 2,6-dibromo-p-cresol is performed at 15° to 30° C and immediately afterwards side-chain bromination at 160° C, and, after the addition of water, the formed 4-hydroxy-3,5-dibromobenzal bromide is saponified at 100° C.

The process according to the invention can be performed both discontinuously and continuously. In the case of the continuous procedure, nucleus bromination and side-chain bromination are in each case advantageously performed in cascade agitators, whilst, finally, hydrolysis is performed preferably using the counter-current principle.

Compared with the known process starting with p-cresol for the production of 4-hydroxy-3,5-dibromobenzaldehyde, the process of the invention has the advantage that a smaller number of steps are required. At the same time, there is obtained a better yield of 4-hydroxy-3,5-dibromobenzaldehyde. A further advantage of the process of the invention is that all steps of the process can be performed in the same solvents without an intermediate having to be isolated. The only by-product occurring in appreciable amounts is hydrogen bromide. Bromine can easily be recovered from this and can be used again for bromination.

The regeneration of bromine from the occurring hydrobromic acid can be performed, using known processes, by the action of chlorine or hydrogen peroxide. For ecological reasons, regeneration with hydrogen peroxide is to be preferred, since in this case merely water is discharged from the plant.

The process according to the invention is further illustrated in the following with reference to the attached drawing (FIG. 1).

In the stirrer vessel 11 are placed 900 kg of p-cresol and 750 kg of o-dichlorobenzene, and at 20° to 30° C there is added in the course of 2 hours 2660 kg of bromine. After completion of the addition, stirring is maintained for 2 hours at 20° to 30° C. The hydrogen bromide formed during the reaction is absorbed in the packed column 12 in water, and is fed to the bromine regeneration stage.

The reaction mixture containing 2,6-dibromo-p-cresol is transferred from stirrer vessel 11 to stirrer vessel 21 and heated to 150° to 160° C. At this temperature there is added within 2 hours 2740 kg of bromine.

After completion of the addition, stirring is subsequently carried out for 3 hours at 150° to 160° C. The hydrogen bromide formed during the reaction is washed free from bromine in the packed column 22 by countercurrent extraction with, in all, 2800 kg of o-dichlorobenzene; the resulting solution of bromine in o-dichlorobenzene is fed back to the stirrer vessel 21, while the bromine-free hydrogen bromide is supplied to the absorption column 12.

The reaction mixture from stirrer vessel 21 is transferred to stirrer vessel 31, and stirred with 4000 kg of water for 1 hour at 100° C. The stirrer is afterwards switched off and the layers are separated. The upper aqueous layer is fed to the buffer vessel 32, cooled to room temperature, and in filter 34 freed from precipitated 4-hydroxy-3,5-dibromobenzaldehyde (about 5 kg per 1000 kg of HBr solution). The hydrobromic acid obtained passes to the bromine regeneration stage.

The resulting solution of 4-hydroxy-3,5-dibromobenzaldehyde in o-dichlorobenzene can be used directly for further reaction with hydroxylamine. If required, however, it is also possible to isolate the 4-hydroxy-3,5-dibromobenzaldehyde from this solution by crystallisation.

The yield of 4-hydroxy-3,5-dibromobenzaldehyde is 1850 kg (79% of theory relative to p-cresol).

EXAMPLE 1

320 g (2 moles) of bromine is added dropwise in the course of 2 hours at 20° to 30° C, with stirring, to a solution of 108 g (1 mole) of p-cresol in 90 g of o-dichlorobenzene. The reaction mixture is then stirred for 2 hours at 20° to 30° C, and afterwards heated to 150° to 160° C. There is subsequently added dropwise at this temperature, during 2 hours, 328 g (2.05 moles) of bromine. After the addition of bromine, the reaction mixture is stirred for 3 hours at 150° to 160° C. The hydrogen bromide escaping from the reaction mixture is washed free from bromine by countercurrent extraction with a total amount of 330 g of o-dichlorobenzene, and the resulting solution of bromine in o-dichlorobenzene is added to the reaction mixture. To effect hydrolysis of the formed 4-hydroxy-3,5-dibromobenzal bromide, there is added to the reaction mixture 500 g of water; the whole is stirred for 2 hours at 100° C, and the layers are separated. The resulting solution of 4-hydroxy-3,5-dibromobenzaldehyde in o-dichlorobenzene can be processed in various ways:

a. The resulting solution of 4-hydroxy-3,5-dibromobenzaldehyde in o-dichlorobenzene is cooled to room temperature, whereupon 4-hydroxy-3,5-dibromobenzaldehyde crystallises out. The crystalline aldehyde is separated by filtration, washed with o-dichlorobenzene and dried in vacuo at 100° C. There is obtained 218 g (78% of theory relative to p-cresol) of 4-hydroxy-3,5-dibromobenzaldehyde, m.p. 182° to 184° C.

b. 500 parts of water are added, with stirring, to the resulting solution of 4-hydroxy-3,5-dibromobenzaldehyde in o-dichlorobenzene and the pH is adjusted to 7.5 by addition of sodium hydroxide solution, whereupon the hydroxyaldehyde passes as sodium salt into the aqueous phase. After separation of o-dichlorobenzene, 4-hydroxy-3,5-dibromobenzaldehyde is precipitated at pH 3 by the addition of sulphuric acid; it is filtered, washed with water and dried at 100° C. There is obtained 224 g (80% of theory relative to p-cresol) of 4-hydroxy-3,5-dibromobenzaldehyde, m.p. 182°–184° C.

c. 500 ml of water and 70 parts of hydroxylaminesulphate are added, with stirring, to the resulting solution of 4-hydroxy-3,5-dibromobenzaldehyde in o-dichlorobenzene. The reaction mixture is brought to pH 5 with sodium hydroxide solution, and subsequently stirred for 1 hour at 80° to 90° C. 4-Hydroxy-3,5-dibromobenzaldoxime precipitates in crystalline form from the reaction mixture. It is filtered off at room temperature, washed with o-dichlorobenzene and water, and dried at 100° C in vacuo. There is obtained 230 g (78% of theory relative to p-cresol) of 4-hydroxy-3,5-dibromobenzaldoxime, which melts at 190°–194° C with decomposition.

EXAMPLE 2

108 g (1 mole) of p-cresol is reacted, in a manner analogous to that in Example 1, in 400 g of o-dichlorobenzene at 20° to 30° C with 320 g (2 moles) of bromine. The formed 2,6-dibromo-p-cresol is then brominated in the side-chain at 100° C, with exposure to UV light for 1 hour, by the addition of 328 g (2.05 moles) of bromine. Hydrolysis of the formed 4-hydroxy-3,5-dibromobenzalbromide is performed by a procedure analogous to that in Example 1. The resulting solution of 4-hydroxy-3,5-dibromobenzaldehyde in o-dichlorobenzene is processed by methods analogous to methods (a) to (c) described in Example 1. The following results are obtained:

a. 230 g (82% of theory) of 4-hydroxy-3,5-dibromobenzaldehyde;

b. 238 g (85% of theory) of 4-hydroxy-3,5-dibromobenzaldehyde;

c. 245 g (83% of theory) of 4-hydroxy-3,5-dibromobenzaldoxime.

EXAMPLE 3

320 g (2 moles) of bromine is added dropwise at 50° C within 2 hours, with stirring, to a melt of 108 g (1 mole) of p-cresol. The melt is subsequently stirred at 50° C for 1 hour, and afterwards heated to 150°–160° C. At this temperature there is added below the surface, in the course of 3 hours, 328 g (2.05 moles) of bromine. After addition of the bromine, the melt is stirred at 150°–160° C for 3 hours. For hydrolysis of the formed 4-hydroxy-3,5-dibromobenzal bromide there is added 750 g of water, and stirring is maintained at 100° C for 4 hours. The resulting suspension of 4-hydroxy-3,5-dibromobenzaldehyde is filtered off at room temperature, washed neutral with water, and dried at 100° C in vacuo. There is obtained 280 g of crude aldehyde containing approx. 80% of 4-hydroxy-3,5-dibromobenzaldehyde (about 80% of theory, relative to p-cresol). The aldehyde obtained can be used, optionally after purification, for further reactions.

We claim:

1. A process for the production of 4-hydroxy-3,5-dibromobenzaldehyde which comprises the steps of reacting p-cresol with bromine at a temperature of from about 0° to 50° C in a molar ratio of about 1:2 to form 2,6-dibromo-p-cresol; reacting said 2,6-dibromo-p-cresol with about 2.0 moles of bromine at a temperature of from about 120° to 180 ° C. by means of side-chain bromination to form 4-hydroxy-3,5-dibromobenzal bromide; and hydrolyzing said bromide with water to yield said 4-hydroxy-3,5-dibromobenzaldehyde.

2. Process according to claim 1, wherein the individual steps of the process are performed in a halogenated hydrocarbon as solvent.

3. Process according to claim 2, wherein the solvent used is chlorobenzene, bromobenzene, o-dichlorobenzene, chloroform or carbon tetrachloride.

4. Process according to claim 3, wherein the solvent used is o-dichlorobenzene.

5. Process according to claim 1, wherein said hydrolysis is conducted at a temperature of between 90° and 100° C.

6. Process according to claim 2, wherein the ratio of organic solvent to water is 2:1 to 1:2.

7. Process according to claim 2, wherein o-dichlorobenzene is employed as solvent, bromination to give 2,6-dibromo-p-cresol is performed at between 15° and 30° C, immediately afterwards side-chain bromination is conducted at between 150° and 160° C, and the formed 4-hydroxy-3,5-dibromobenzalbromide is saponified at 100° C after the addition of water.

* * * * *

UNITED STATES PATENT AND TRADEMARK OFFICE
CERTIFICATE OF CORRECTION

PATENT NO. : 3,996,291
DATED : December 7, 1976
INVENTOR(S) : Henri Dietrich et al It is certified that error appears in the above-identified patent and that said Letters Patent are hereby corrected as shown below:

In the heading under Foreign Application Priority Data add:

--and Swiss application no. 228/75, filed January 9, 1975--

Signed and Sealed this

Thirteenth Day of September 1977

[SEAL]

Attest:

RUTH C. MASON
Attesting Officer

LUTRELLE F. PARKER
Acting Commissioner of Patents and Trademarks